United States Patent
Sugiyama et al.

(10) Patent No.: US 7,692,048 B2
(45) Date of Patent: Apr. 6, 2010

(54) METHOD FOR PRODUCING FLUORINE-CONTAINING HALIDE

(75) Inventors: Akinari Sugiyama, Settsu (JP);
Kazuyoshi Ichihara, Settsu (JP);
Noriyuki Shinoki, Settsu (JP); Toshiya Mantani, Settsu (JP); Masahiro Kondou, Settsu (JP)

(73) Assignee: Daikin Industries, Ltd., Osaka-shi (JP)

( * ) Notice: Subject to any disclaimer, the term of this patent is extended or adjusted under 35 U.S.C. 154(b) by 496 days.

(21) Appl. No.: 10/593,322

(22) PCT Filed: Mar. 11, 2005

(86) PCT No.: PCT/JP2005/004302

§ 371 (c)(1),
(2), (4) Date: Sep. 18, 2006

(87) PCT Pub. No.: WO2005/090270

PCT Pub. Date: Sep. 29, 2005

(65) Prior Publication Data

US 2007/0185355 A1    Aug. 9, 2007

(30) Foreign Application Priority Data

Mar. 23, 2004  (JP) ............................ 2004-085295
Jul. 8, 2004   (JP) ............................ 2004-201299

(51) Int. Cl.
*C07C 19/08* (2006.01)
(52) U.S. Cl. ..................... 570/140; 570/141
(58) Field of Classification Search ............. 570/140, 570/141
See application file for complete search history.

(56) References Cited

U.S. PATENT DOCUMENTS

| 3,560,568 A | * | 2/1971 | Resnick | ............... 562/111 |
| 4,912,269 A | * | 3/1990 | Drivon et al. | ............... 570/142 |
| 5,057,633 A | * | 10/1991 | Drivon et al. | ............... 570/142 |

FOREIGN PATENT DOCUMENTS

| JP | 64-13037 | | 1/1989 |
| JP | 2-83364 | | 3/1990 |
| JP | 3-34937 | | 2/1991 |
| JP | 10-287596 | | 10/1998 |
| JP | 2004-244401 | * | 9/2004 |

OTHER PUBLICATIONS

Storzer et al., {Two fluorinated, fluorosulfonyl-containing hypochlorites and their alkali-metal precursors, Inorganic Chemistry (1991), 30(25), 4821-4826}.*
Oudrhiri-Hassani et al; "Thermolyse Des Halogenures de Perfluoroalcanesulfonyle;" J. Fluorine Chem. 25 (1984) pp. 491-504.

* cited by examiner

*Primary Examiner*—Sikarl A Witherspoon
*Assistant Examiner*—Chukwuma O Nwaonicha
(74) *Attorney, Agent, or Firm*—Kratz, Quintos & Hanson, LLP

(57) ABSTRACT

The present invention provides a method for producing a fluorine-containing halide, comprising reacting a fluorine-containing sulfonyl halide or fluorine-containing disulfonyl chloride with a metal halide or metal component in the present or absence of a solvent. In accordance with the present invention, a fluorine-containing bromide, fluorine-containing iodide or fluorine-containing chloride can be readily produced in high yield at low cost, using an industrially advantageous process.

20 Claims, No Drawings

METHOD FOR PRODUCING FLUORINE-CONTAINING HALIDE

TECHNICAL FIELD

The present invention relates to a method for producing a fluorine-containing halide.

BACKGROUND ART

Fluorine-containing halides represented by chemical formulae $R_{fl}Br$, $R_{fl}I$ and $R_{fl}Cl$, wherein $R_{fl}$ is a saturated or unsaturated fluorine-containing group, are compounds useful as the intermediates for chemicals, pharmaceuticals, agrochemicals, resins and the like. For example, fluorine-containing saturated alkyl bromides are used as blood substitutes, perfluoroalkylating agents and the like. Fluorine-containing unsaturated bromides, fluorine-containing unsaturated iodides and the like are also useful as monomer components for the production of functional materials, because they have replaceable bromine or iodine as a functional group.

A method for producing a fluorine-containing halide is known which converts a sulfonyl chloride represented by chemical formula $R_{fl}SO_2Cl$ to a fluorine-containing bromide represented by chemical formula $R_{fl}Br$, in accordance with reaction formula 1 shown below (see, for example, Patent Document 1 listed below):

formula 1

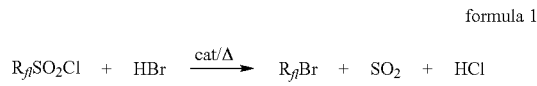

This method, however, employs HBr, a corrosive gas, at high pressures, and produces as a byproduct HCl, which is similarly a corrosive gas, thus causing corrosion of the reaction vessel. Moreover, the reaction has to be carried out in the absence of water, making it difficult to handle reagents. In addition, the reaction needs to be carried out in a high temperature ranging from about 90 to about 150° C.

Another method is known which produces $R_{fl}Br$ in accordance with reaction formula 2 shown below (see Patent Document 2 listed below):

$R_{fl}SO_2Cl$+quaternary (ammonium or phosphonium) bromide→$R_{fl}Br$+$SO_2$+quaternary (ammonium or phosphonium) chloride      formula 2

The drawbacks of this method are that the use of an expensive quaternary (ammonium or phosphonium) bromide as a starting material is necessary, and that a large amount of byproduct, i.e., a quaternary (ammonium or phosphonium) chloride, is produced as a waste material.

Moreover, a method is known for synthesizing a fluorine-containing chloride represented by chemical formula $R_{fl}Cl$ using a sulfonyl chloride represented by chemical formula $R_{fl}SO_2Cl$ as a starting material, wherein $R_{fl}Cl$ is produced in accordance with the reaction formula shown below (see Patent Document 3 shown below):

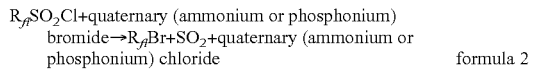

This method, however, is also industrially disadvantageous in that the reaction has to be carried out at a high temperature.

No process is known for synthesizing a fluorine-containing iodide represented by $R_{fl}I$ using a sulfonyl chloride represented by chemical formula $R_{fl}SO_2Cl$ as a starting material.

[Patent Document 1] U.S. Pat. No. 4912269
[Patent Document 2] U.S. Pat. No. 5057633
[Patent Document 3] Journal of Fluorine Chemistry, 25 (1984), 491-504

DISCLOSURE OF THE INVENTION

Problem to be Solved by the Invention

A principal object of the present invention is to provide a simple and low-cost method for producing a fluorine-containing halide in good yield by an industrially advantageous process.

Means for Solving the Problem

The present inventors conducted extensive research in order to achieve the aforementioned object, and conceived a method in which a fluorine-containing sulfonyl halide is used as a starting material, and the starting material is reacted with a specific metal or a compound containing such a metal, thereby allowing the target fluorine-containing bromide, fluorine-containing iodide or fluorine-containing chloride to be produced in high yield at a relatively low reaction temperature, i.e., about room temperature, using the low-cost and readily available starting material. This finding has led to the accomplishment of the present invention.

The present invention provides methods for producing fluorine-containing halides as itemized below.

1. A method for producing a fluorine-containing halide, comprising reacting a fluorine-containing sulfonyl halide with a metal halide in the presence or absence of a solvent, the fluorine-containing sulfonyl halide being represented by general formula (1):

(1)

wherein $R^1$, $R^2$ and $R^3$ are the same or different, each representing a halogen atom, a hydrogen atom or a monovalent hydrocarbon group which may contain one or more atoms of one or more kinds selected from fluorine, oxygen, nitrogen and sulfur atoms; at least one of $R^1$, $R^2$ and $R^3$ is a halogen atom; Z is Cl or F; provided that when none of $R^1$, $R^2$ and $R^3$ is a fluorine atom, at least one of $R^1$, $R^2$ and $R^3$ is a monovalent fluorine-containing hydrocarbon group, and when Z is F, $R_1$ and $R_3$ are both fluorine atoms and $R_2$ is a $CF_2$=$CFOCF_2$— group;

the metal halide being represented by general formula $M^1X$, wherein $M^1$ is Ma or $(Mb)_{1/2}$, Ma being an alkali metal, Mb being an alkaline earth metal, and X being Br or I;

the fluorine-containing halide being represented by the general formula shown below:

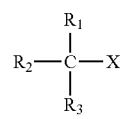

wherein $R^1$, $R^2$, $R^3$ and X are the same as above.

2. The method for producing a fluorine-containing halide according to item 1, wherein the fluorine-containing sulfonyl halide represented by general formula (1) is a compound represented by general formula (1a):

$R^4CF_2SO_2Cl$      (1a)

wherein $R^4$ is a halogen atom, a hydrogen atom or a monovalent hydrocarbon group which may contain one or more atoms of one or more kinds selected from fluorine, oxygen, nitrogen and sulfur atoms.

3. The method for producing a fluorine-containing halide according to item 1, wherein the fluorine-containing sulfonyl halide represented by general formula (1) is a compound represented by general formula $Y(CF_2)_n$—$SO_2Cl$ wherein Y is a halogen atom, —$SO_2F$ or —$CCl_3$, and n is an integer from 1 to 9; a compound represented by general formula $CF_2$=$CF(CF_2)_e(OCF_2CF(CF_3))_gO(CF_2)_h$—$SO_2Cl$ wherein e is an integer from 0 to 2, g is an integer from 0 to 3, and h is an integer from 1 to 6; or a compound represented by general formula $CF_2$=$CFOCF_2CF_2SO_2F$.

4. The method according to item 1, wherein the metal halide represented by chemical formula $M^1X$ is an alkali metal bromide or alkali metal iodide.

5. The method according to item 1, wherein the reaction is carried out in a polar solvent.

6. A method for producing a fluorine-containing chloride, comprising reacting a fluorine-containing sulfonyl chloride in the presence or absence of a solvent with at least one member selected from the group consisting of metals belonging to periods 4 to 7 of groups 3 to 16 in the periodic table and compounds containing any of such metals, the fluorine-containing sulfonyl chloride being represented by general formula (1'):

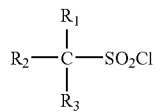

(1')

wherein $R^1$, $R^2$ and $R^3$ are the same or different, each representing a halogen atom, a hydrogen atom or a monovalent hydrocarbon group which may contain one or more atoms of one or more kinds selected from fluorine, oxygen, nitrogen and sulfur atoms; and at least one of $R^1$, $R^2$ and $R^3$ is a halogen atom; provided that when none of $R^1$, $R^2$ and $R^3$ is a fluorine atom, at least one of $R^1$, $R^2$ and $R^3$ is a monovalent fluorine-containing hydrocarbon group;

the fluorine-containing chloride being represented by the general formula shown below:

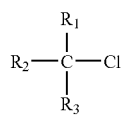

wherein $R^1$, $R^2$ and $R^3$ are the same as above.

7. The method for producing a fluorine-containing chloride according to item 6, wherein the fluorine-containing sulfonyl chloride represented by general formula (1') is a compound represented by general formula (1a):

$R^4CF_2SO_2Cl$ (1a)

wherein $R^4$ is a halogen atom, a hydrogen atom or a monovalent hydrocarbon group which may contain one or more atoms of one or more kinds selected from fluorine, oxygen, nitrogen and sulfur atoms.

8. The method for producing a fluorine-containing chloride according to item 6, wherein the fluorine-containing sulfonyl chloride represented by general formula (1') is a compound represented by general formula $Y(CF_2)_n$—$SO_2Cl$ wherein Y is a halogen atom, —$SO_2F$ or —$CCl_3$, and n is an integer from 1 to 9; or a compound represented by general formula $CF_2$=$CF(CF_2)_e(OCF_2CF(CF_3))_gO(CF_2)_h$—$SO_2Cl$ wherein e is an integer from 0 to 2, g is an integer from 0 to 3, and h is an integer from 1 to 6.

9. The method according to item 6, wherein the metals belonging to periods 4 to 7 of groups 3 to 16 in the periodic table are Cu, Pt, Pd, Ni, Zn and Fe, and the compounds containing any of metals belonging to periods 4 to 7 of groups 3 to 16 in the periodic table are compounds containing Cu, Fe, Ni, Co, Pd. Ti or Pb as a metal component.

10. The method according to item 6, wherein the reaction is carried out in a polar solvent.

11. A method for producing a fluorine-containing halide, comprising reacting a fluorine-containing disulfonyl chloride with a metal halide in the presence or absence of a solvent, the fluorine-containing disulfonyl chloride being represented by general formula (2):

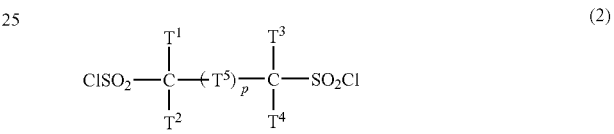

(2)

wherein $T^1$, $T^2$, $T^3$ and $T^4$ are the same or different, each representing a halogen atom, hydrogen atom or monovalent hydrocarbon group which may contain one or more atoms of one or more kinds selected from fluorine, oxygen, nitrogen and sulfur atoms; at least one of $T^1$, $T^2$, $T^3$ and $T^4$ is a halogen atom; $T^5$ is a bivalent hydrocarbon group which may contain one or more atoms of one or more kinds selected from fluorine, oxygen, nitrogen and sulfur atoms; and p is 0 or 1; provided that at least one of $T^1$ and $T^2$ is a monovalent fluorine-containing hydrocarbon group when neither $T^1$ nor $T^2$ is a fluorine atom, and at least one of $T^3$ and $T^4$ is a monovalent fluorine-containing hydrocarbon group when neither $T^3$ nor $T^4$ is a fluorine atom;

the metal halide being represented by general formula $M^1X$, wherein $M^1$ is Ma or $(Mb)_{1/2}$, Ma being an alkali metal, Mb being an alkaline earth metal, and X being Br or I;

the fluorine-containing halide being represented by general formula:

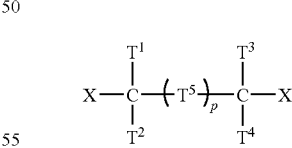

wherein $T^1$, $T^2$, $T^3$, $T^4$, $T^5$, X and p are the same as above.

12. The method for producing a fluorine-containing halide according to item 11, wherein the fluorine-containing disulfonyl chloride represented by general formula (2) is a compound represented by general formula (2a):

$ClSO_2$—$F_2C$-$(T^5)_p$-$CF_2$—$SO_2Cl$ (2a)

wherein $T^5$ is a bivalent hydrocarbon group which may contain one or more atoms of one or more kinds selected from fluorine, oxygen, nitrogen and sulfur atoms; and p is 0 or 1.

13. The method for producing a fluorine-containing halide according to item 11, wherein the fluorine-containing disulfonyl chloride represented by general formula (2) is a compound represented by general formula $ClSO_2(CF_2)_pSO_2Cl$, wherein p is an integer from 2 to 9.

14. The method according to item 11, wherein the metal halide represented by chemical formula $M^1X$ is an alkali metal bromide or alkali metal iodide.

15. The method according to item 11, wherein the reaction is carried out in a polar solvent.

16. A method for producing a fluorine-containing chloride, comprising reacting a fluorine-containing disulfonyl chloride in the presence or absence of a solvent with at least one member selected from the group consisting of metals belonging to periods 4 to 7 of groups 3 to 16 in the periodic table and compounds containing any of such metals, the fluorine-containing disulfonyl chloride being represented by general formula (2):

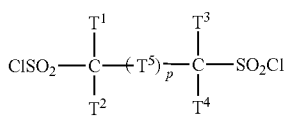

(2)

wherein $T^1$, $T^2$, $T^3$ and $T^4$ are the same or different, each representing a halogen atom, hydrogen atom or monovalent hydrocarbon group which may contain one or more atoms of one or more kinds selected from fluorine, oxygen, nitrogen and sulfur atoms; at least one of $T^1$, $T^2$, $T^3$ and $T^4$ is a halogen atom; $T^5$ is a bivalent hydrocarbon group which may contain one or more atoms of one or more kinds selected from fluorine, oxygen, nitrogen and sulfur atoms; and p is 0 or 1; provided that at least one of $T^1$ and $T^2$ is a monovalent fluorine-containing hydrocarbon group when neither $T^1$ nor T2 is a fluorine atom, and at least one of $T^3$ and $T^4$ is a monovalent fluorine-containing hydrocarbon group when neither $T^3$ nor $T^4$ is a fluorine atom;

the fluorine-containing chloride being represented by general formula:

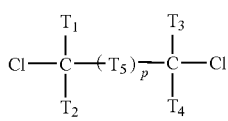

wherein $T^1$, $T^2$, $T^3$, $T^4$, $T^5$ and p are the same as above.

17. The method for producing a fluorine-containing chloride according to item 16, wherein the fluorine-containing disulfonyl chloride represented by general formula (2) is a compound represented by general formula (2a):

(2a)

wherein $T^5$ is a bivalent hydrocarbon group which may contain one or more atoms of one or more kinds selected from fluorine, oxygen, nitrogen and sulfur atoms; and p is 0 or 1.

18. The method for producing a fluorine-containing chloride according to item 16, wherein the fluorine-containing disulfonyl chloride represented by general formula (2) is a compound represented by general formula $ClSO_2(CF_2)_pSO_2Cl$, wherein p is an integer from 2 to 9.

19. The method according to item 16, wherein the metals belonging to periods 4 to 7 of groups 3 to 16 in the periodic table are Cu, Pt, Pd, Ni, Zn and Fe, and the compounds containing any of metals belonging to periods 4 to 7 of groups 3 to 16 in the periodic table are compounds containing Cu, Fe, Ni, Co, Pd, Ti or Pb as a metal component.

20. The method according to item 16, wherein the reaction is carried out in a polar solvent.

In accordance with the method of the present invention, a fluorine-containing sulfonyl halide or a fluorine-containing disulfonyl chloride is used as a starting material.

The fluorine-containing sulfonyl halide is represented by general formula (1).

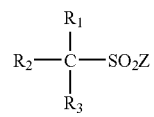

(1)

The fluorine-containing disulfonyl chloride is represented by general formula (2).

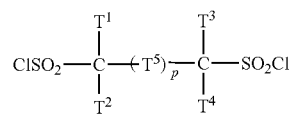

(2)

In the fluorine-containing sulfonyl halide represented by general formula (1) shown above, $R^1$, $R^2$ and $R^3$ are the same or different, each representing a halogen atom, hydrogen atom or monovalent hydrocarbon group; at least one of $R^1$, $R^2$ and $R^3$ is a halogen atom, and Z is Cl or F; provided that when Z is F, $R_1$ and $R_3$ are both fluorine atoms and $R_2$ is a $CF_2$=$CFOCF_2$— group.

Examples of halogen atoms used herein are F, Cl, Br, and I. The monovalent hydrocarbon group may be a linear, branched or cyclic, saturated or unsaturated aliphatic hydrocarbon group, or an aromatic hydrocarbon group. Such a hydrocarbon group may contain one or more atoms of one or more kinds selected from hetero atoms, such as fluorine, oxygen, nitrogen and sulfur atoms, and may further contain one or more cyclic groups, such as aromatic, alicyclic and heterocyclic groups.

When none of $R_1$, $R_2$ and $R_3$ is a fluorine atom, at least one of $R_1$, $R_2$ and $R_3$ is a monovalent fluorine-containing hydrocarbon group. In this case, the monovalent fluorine-containing hydrocarbon group may be a completely fluorinated perfluoro group or may be such that only some of the carbon atoms are fluorinated.

Among the fluorine-containing sulfonyl halides represented by general formula (1) shown above, specific examples of those wherein Z is Cl include compounds represented by general formula (1a):

(1a)

wherein $R^4$ is a halogen atom, hydrogen atom or monovalent hydrocarbon group which may contain one or more atoms of one or more kinds selected from fluorine, oxygen, nitrogen and sulfur atoms. The use of such a compound as a starting material permits the target material to be produced in good yield at relatively low temperatures.

Specific examples of fluorine-containing sulfonyl halides according to general formula (1a) include compounds represented by general formulae shown below:

$$CF_2XCFX(CF_2)_l A\{CF_2CF(CF_3)O\}_m(CF_2)_n SO_2Cl \quad (i)$$

wherein X is F, Cl or Br; A is O, S or NH; l is an integer from 0 to 4; m is an integer from 0 to 3; and n is an integer from 1 to 8;

$$Y(CF_2)_l A\{CF_2CF(CF_3)O\}_m(CF_2)_n SO_2Cl \quad (ii)$$

wherein Y is H, a halogen atom, $CCl_3$, $-CO_2M^2$ (wherein $M^2$ is Ma or $(Mb)_{1/2}$, Ma being an alkali metal, and Mb being an alkaline earth metal), or an aromatic group (which may additionally contain one or more substituents); A is O, S or NH; l is an integer from 1 to 8; m is an integer from 0 to 3; and n is an integer from 1 to 8; and $$Y(CF_2CF_2O)_l(CF_2)_m SO_2Cl \quad (iii)$$

wherein Y is H, a halogen atom, $-CO_2M^2$ (wherein $M^2$ is Ma or $(Mb)_{1/2}$, Ma being an alkali metal, and Mb being an alkaline earth metal), or an aromatic group (which may additionally contain one or more substituents); l is an integer from 0 to 50; and m is an integer from 1 to 20.

Examples of aromatic groups for use in compounds represented by formulae shown above may include phenyl, naphthyl, anthryl and the like.

Examples of substituents for aromatic groups include $-NO_2$, $-CN$, $-NH_2$, $-CH_3$, $-CH_2OH$, $-Br$, $-I$, $-Cl$, $-CO_2H$, $-SO_3H$, $-CO_2Na$, $-CONH_2$, $-CO_2N(Et)_2$, and the like.

Specific examples of compounds according to the general formulae shown above include the following:

Compounds represented by $CF_2XCFX(CF_2)_l A\{CF_2CF(CF_3)O\}_m(CF_2)_n SO_2Cl$: $CF_2ClCFClOCF_2CF_2SO_2Cl$, $CF_2ClCFClOCF_2CF_2CF_2SO_2Cl$, $CF_2ClCFClOCF_2CF_2CF_2CF_2SO_2Cl$, $CF_2ClCFClOCF_2CF(CF_3)OCF_2CF_2SO_2Cl$, $CF_2ClCFCl\{CF_2CF(CF_3)O\}_2OCF_2CF_2SO_2Cl$, $CF_2ClCFClOCF_2CF(CF_3)OCF_2CF_2CF_2SO_2Cl$, and $CF_2ClCFClOCF_2CF(CF_3)OCF_2CF_2CF_2CF_2SO_2Cl$;

Compounds represented by $Y(CF_2)_l A\{CF_2CF(CF_3)O\}_m(CF_2)_n SO_2Cl$: $Y(CF_2)_2 O(CF_2)_2 SO_2Cl$, $Y(CF_2)_2 O(CF_2)_3 SO_2Cl$, $Y(CF_2)_2 O SO_2Cl$, $Y(CF_2)_4 O(CF_2)_2 SO_2Cl$, $Y(CF_2)_6 O(CF_2)_2 SO_2Cl$, and $Y(CF_2)_2 O(CF_2)_4 SO_2Cl$ wherein Y is H, F, Cl, Br, I or $CF_2=CF-$;

$NaO_2C(CF_2)_m O(CF_2)_n SO_2Cl$
wherein n is an integer from 1 to 8, and m is an integer from 1 to 8;

$CCl_3(CF_2)_m O(CF_2)_n SO_2Cl$
wherein n is an integer from 1 to 8, and m is an integer from 1 to 8; and $\phi$-$(CF_2)_m O(CF_2)_n SO_2Cl$
wherein $\phi$ is Ph (phenyl), Ph-$NO_2$, Ph-CN, Ph-$NH_2$, Ph-$CH_3$, Ph-$(CH_3)_2$, Ph-$CH_2OH$, Ph-Br, Ph-$Br_2$, Ph-I, Ph-$I_2$, Ph-Cl, Ph-$Cl_2$, Ph-$CO_2H$, Ph-$(CO_2H)_2$, Ph-$SO_3H$, Ph-$CO_2Na$, Ph-$(CO_2Na)_2$, Ph-$CONH_2$, Ph-$CO_2N(Et)_2$, naphthyl, anthryl or like aromatic group; n is an integer from 1 to 8; m is an integer from 1 to 8; and Z is F or Cl; and Compounds represented by $Y(CF_2CF_2O)_l(CF_2)_m SO_2Cl$: $ICF_2CF_2OCF_2CF_2OCF_2CF_2SO_2Cl$, $ICF_2CF_2OCF_2CF_2OCF_2CF_2CF_2SO_2Cl$, $ICF_2CF_2OCF_2CF_2OCF_2CF_2CF_2CF_2SO_2Cl$, $ICF_2SO_2Cl$, $ICF_2CF_2SO_2Cl$, $ICF_2CF_2CF_2SO_2Cl$, $F_3SO_2Cl$, $CF_3CF_2SO_2Cl$, $CF_3(CF_2)_6SO_2Cl$, $ClO_2SCF_2$-$\phi$, $ClO_2SCF_2CF_2$-$\phi$, and $ClO_2SCF_2CF_2OCF_2CF_2$-$\phi$, wherein $\phi$ is Ph (phenyl), Ph-$NO_2$, Ph-CN, Ph-$NH_2$, Ph-$CH_3$, Ph-$(CH_3)_2$, Ph-$CH_2OH$, Ph-Br, Ph-$Br_2$, Ph-I, Ph-$I_2$, Ph-Cl, Ph-$Cl_2$, Ph-$CO_2H$, Ph-$(CO_2H)_2$, Ph-$SO_3H$, Ph-$CO_2Na$, Ph-$(CO_2Na)_2$, Ph-$CONH_2$, Ph-$CO_2N(Et)_2$, naphthyl, anthryl or like aromatic group.

Among fluorine-containing sulfonyl halides represented by general formula (1) shown above wherein Z is Cl, compounds represented by general formula $Y(CF_2)_n$—$SO_2Cl$, wherein Y is a halogen atom, $-SO_2F$ or $-CCl_3$, and n is an integer from 1 to 9; and compounds represented by general formula $CF_2=CF(CF_2)_e(OCF_2CF(CF_3))_g O(CF_2)_h$—$SO_2Cl$, wherein e is an integer from 0 to 2, g is an integer from 0 to 3, and h is an integer from 1 to 6, are particularly preferable in terms of the ease of separation and purification of the resulting products. In compounds represented by general formula $Y(CF_2)_n$—$SO_2Cl$, Y is preferably a fluorine atom, and n is preferably an integer from 1 to 8.

Specific examples of compounds according to each of the aforementioned general formulae are as follows:

Compounds represented by $Y(CF_2)_n$—$SO_2Cl$: $Y(CF_2)_2 SO_2Cl$, $Y(CF_2)_3 SO_2Cl$, $Y(CF_2)_4 SO_2Cl$, $Y(CF_2)_5 SO_2Cl$, $Y(CF_2)_6 SO_2Cl$, and the like, wherein Y is a halogen atom, $CCl_3$ or $SO_2F$; and Compounds represented by $CF_2=CF(CF_2)_e(OCF_2CF(CF_3))_g O(CF_2)_h$—$SO_2Cl$: $CF_2=CFOCF_2CF_2SO_2Cl$, $CF_2=CFOCF_2CF_2CF_2SO_2Cl$, $CF_2=CFOCF_2CF_2CF_2CF_2SO_2Cl$, $CF_2=CFOCF(CF_3)OCF_2CF_2SO_2Cl$, $CF_2=CF\{CF_2CF(CF_3)O\}_2 OCF_2CF_2SO_2Cl$, $CF_2=CFOCF_2CF(CF_3)OCF_2CF_2CF_2SO_2Cl$, and $CF_2=CFOCF_2CF(CF_3)OCF_2CF_2CF_2CF_2SO_2Cl$.

Among fluorine-containing sulfonyl halides represented by general formula (1) shown above, compounds wherein Z is F can be represented by chemical formula $CF_2=CFOCF_2CF_2$—$SO_2F$.

In the fluorine-containing disulfonyl chloride represented by general formula (2), $T^1$, $T^2$, $T^3$ and $T^4$ may be the same or different, each representing a halogen atom, hydrogen atom or monovalent hydrocarbon group; at least one of $T^1$, $T^2$, $T^3$ and $T^4$ is a halogen atom; $T^5$ is a bivalent hydrocarbon group; and p is 0 or 1.

Examples of halogen atoms used herein are F, Cl, Br, and I. The monovalent and bivalent hydrocarbon groups may each be a linear, branched or cyclic, saturated or unsaturated aliphatic hydrocarbon group, or an aromatic hydrocarbon group. Such a hydrocarbon group may contain one or more atoms of one or more kinds selected from hetero atoms, such as fluorine, oxygen, nitrogen and sulfur atoms, and may further contain one or more cyclic groups, such as aromatic, alicyclic and heterocyclic groups.

When neither $T^1$ nor $T^2$ is a fluorine atom, at least one of $T^1$ and $T^2$ is a monovalent fluorine-containing hydrocarbon group, and when neither $T^3$ nor $T^4$ is a fluorine atom, at least one of $T^3$ and $T^4$ is a monovalent fluorine-containing hydrocarbon group.

When the monovalent hydrocarbon group and the bivalent hydrocarbon group are fluorine-containing hydrocarbon groups, the fluorine-containing hydrocarbon groups may be completely fluorinated perfluoro groups or may be such that only some of the carbon atoms are fluorinated.

Among the fluorine-containing disulfonyl chlorides represented by general formula (2) above, specific examples of preferable compounds include those represented by general formula (2a):

$$ClSO_2-F_2C-(T^5)_p-CF_2-SO_2Cl \quad (2a)$$

wherein $T^5$ is a bivalent hydrocarbon group which may contain one or more atoms of one or more kinds selected from fluorine, oxygen, nitrogen and sulfur atoms; and p is 0 or 1. The use of such a compound as a starting material permits the target material to be produced in good yield at relatively low temperatures.

Among the fluorine-containing sulfonyl halides represented by general formula (2a) above, compounds represented by general formulae shown below are preferable in terms of the ease of separation and purification of the resulting products:

$$ClO_2S(CF_2)_nSO_2Cl \qquad (i)$$

wherein n is an integer from 2 to 20;

$$ClO_2S(CF_2CF_2A)_l(CF_2)_mSO_2Cl \qquad (ii)$$

wherein A is O, S or NH; l is an integer from 1 to 50; and m is an integer from 1 to 20; and

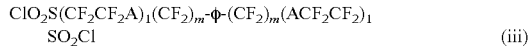
$$ClO_2S(CF_2CF_2A)_l(CF_2)_m\text{-}\phi\text{-}(CF_2)_m(ACF_2CF_2)_l SO_2Cl \qquad (iii)$$

wherein φ is an aromatic group, which may additionally contain one or more substituents at positions to which a $ZO_2S(CF_2CF_2A)_l(CF_2)_m$— group is not linked; l is an integer from 0 to 10; and m is an integer from 1 to 8.

Examples of aromatic groups used in compounds represented by general formulae shown above include phenyl, naphthyl, anthryl and the like, and examples of substituents of such aromatic groups include —$NO_2$, —CN, —$NH_2$, —$CH_3$, —$CH_2OH$, —Br, —I, —Cl, —$CO_2H$, —$SO_3H$, —$CO_2Na$, —$CONH_2$, —$CO_2N(Et)_2$, and the like.

Specific examples of compounds according to general formulae above include the following:

Compounds represented by $ClO_2S(CF_2)_nSO_2Cl$:

$ClO_2SCF_2SO_2Cl$, $ClO_2SCF_2CF_2SO_2Cl$, $ClO_2SCF_2CF_2CF_2SO_2Cl$, and $ClO_2SCF_2CF_2CF_2CF_2CF_2SO_2Cl$;

Compounds represented by $ClO_2S(CF_2CF_2A)_l(CF_2)_mSO_2Cl$:

$ClO_2SCF_2CF_2OCF_2CF_2SO_2Cl$, $ClO_2SCF_2CF_2SCF_2CF_2SO_2Cl$, and $ClO_2SCF_2CF_2OCF_2CF_2CF_2SO_2Cl$; and Compounds represented by $ClO_2S(CF_2CF_2A)_l(CF_2)_m\text{-}\phi\text{-}(CF_2)_m(ACF_2CF_2)_lSO_2Cl$:

$ClO_2SCF_2\text{-}\phi\text{-}CF_2SO_2Cl$, $ClO_2SCF_2CF_2\text{-}\phi\text{-}CF_2CF_2SO_2Cl$, $ClO_2SCF_2CF_2CF_2\text{-}\phi\text{-}CF_2CF_2CF_2SO_2Cl$, $ClO_2SCF_2CF_2CF_2\text{-}\phi\text{-}CF_2CF_2CF_2CF_2SO_2ZCl$, $ClO_2SCF_2CF_2OCF_2CF_2\text{-}\phi\text{-}CF_2CF_2OCF_2CF_2SO_2Cl$, $ClO_2SCF_2CF_2SCF_2CF_2\text{-}\phi\text{-}CF_2CF_2SCF_2CF_2SO_2Cl$, and $ClO_2SCF_2CF_2OCF_2 CF_2CF_2\text{-}\phi\text{-}CF_2CF_2OCF_2CF_2CF_2SO_2Cl$, wherein φ is Ph (phenyl), Ph-$NO_2$, Ph-CN, Ph-$NH_2$, Ph-$CH_3$, Ph-$CH_2OH$, Ph-Br, Ph-I, Ph-Cl, Ph-$CO_2H$, Ph-$SO_3H$, Ph-$CO_2Na$, Ph-$CONH_2$, Ph-$CO_2N(Et)_2$, naphthyl, anthryl or like aromatic group.

Among the fluorine-containing disulfonyl chlorides of general formula (2) shown above, those represented by general formula $ClSO_2(CF_2)_nSO_2Cl$, wherein n is an integer from 2 to 9, are preferable in terms of the ease of separation and purification of the resulting products. Specific examples of compounds represented by this formula include $ClO_2SCF_2CF_2SO_2Cl$, $ClO_2SCF_2CF_2CF_2SO_2Cl$, $ClO_2SCF_2CF_2CF_2CF_2CF_2SO_2Cl$, and the like.

Fluorine-containing sulfonyl halides represented by general formula (1) and fluorine-containing disulfonyl chlorides represented by general formula (2) are both known compounds or compounds readily obtainable by conventional processes.

For producing a fluorine-containing bromide or fluorine-containing iodide in accordance with the present invention, either a fluorine-containing sulfonyl halide of general formula (1) or fluorine-containing disulfonyl chloride of general formula (2) is used as a starting material, and reacted with a metal halide. Usable metal halides are those represented by general formula $M^1X$. In this general formula, $M^1$ is Ma or $(Mb)_{1/2}$; Ma is an alkali metal, such as Li, Na, K, Cs, or the like; Mb is an alkaline earth metal, such as Mg, Ca, Ba, or the like; and X is Br or I. Among such halides, alkali metal bromides and alkali metal iodides, where $M^1$ is an alkali metal and X is Br or I, are preferable, and NaBr, BaI and the like are especially preferable because they are inexpensive.

For producing a fluorine-containing chloride in accordance with the present invention, either a fluorine-containing disulfonyl chloride represented by general formula (2) shown above or a fluorine-containing sulfonyl chloride, i.e., a fluorine-containing sulfonyl halide of general formula (1) wherein Z is Cl, is used as a starting material. The starting fluorine-containing sulfonyl chloride is represented by general formula (1') shown below:

wherein $R^1$, $R^2$ and $R^3$ are the same or different, each representing a halogen atom, a hydrogen atom or a monovalent hydrocarbon group which may contain one or more atoms of one or more kinds selected from fluorine, oxygen, nitrogen and sulfur atoms; and at least one of $R^1$, $R^2$ and $R^3$ is a halogen atom; provided that when none of $R^1$, $R^2$ and $R^3$ is a fluorine atom, at least one of $R^1$, $R^2$ and $R^3$ is a monovalent fluorine-containing hydrocarbon group. Such a starting material is reacted with at least one member selected from the group consisting of metals belonging to periods 4 to 7 of groups 3 to 16 in the periodic table and compounds containing any of such metals. The at least one member selected from the group consisting of such metals and compounds containing any of such metals may, hereinafter, be simply referred to as "metal component(s)".

Specific examples of metals belonging to periods 4 to 7 of groups 3 to 16 in the periodic table include Cu, Ti, V, Cr, Mn, Fe, Co, Ni, Mo, Ru, Rh, Pd, In, Sn, Sb, Ce, Sm, Eu, Yb, Ta, Pt, Os, Ir, Au, Hg, Pb, Bi, Zn and the like, among which Cu, Fe, Ni, Pt, Pd, Zn and the like are preferable in terms of availability. Such metals may be used by themselves or may be supported on a carrier, e.g., a zeolite, activated carbon, etc.

Examples of usable compounds containing any of metals belonging to periods 4 to 7 of groups 3 to 16 in the periodic table include chlorides, nitrates, cyanides, hydroxides, carbonates and the like forms of various metals, among which chlorides and nitrates are preferable in terms of the ease of handling. Compounds which contain typical ligands, e.g., triphenylphosphine ($PPh_3$), β-diketones, etc., are also usable. Specific examples of metals contained in such metal compounds include Cu, Ti, V, Cr, Mn, Fe, Co, Ni, Mo, Ru, Rh, Pd, In, Sn, Sb, Ce, Sm, Eu, Yb, Ta, Pt, Os, Ir, Au, Hg, Pb, Bi, Zn and the like, among which Cu, Fe, Ni, Co, Pd, Ti and Pb are preferable in terms of availability.

The aforementioned metals and metal compounds may be used singly or in combination.

The method of supplying the starting-materials to a reaction vessel is not particularly limited. For example, a fluorine-containing sulfonyl halide or a fluorine-containing disulfonyl chloride may be placed in a reaction vessel together with a metal halide or metal component, or one may be placed in the reaction vessel, and the other may be subsequently added dropwise. In consideration of the heat of reaction, it is preferable to place one in the reaction vessel, and then add the other dropwise.

The ratio of a fluorine-containing sulfonyl halide of general formula (1) or a fluorine-containing disulfonyl chloride of general formula (2) to a metal halide $M^1X$ may be such that the amount of the metal halide $M^1X$ is about 0.1 to about 10 times the stoichiometric amount, and preferably about 1 to about 5 times the stoichiometric amount.

The ratio of a fluorine-containing sulfonyl chloride of general formula (1') or a fluorine-containing disulfonyl chloride of general formula (2) to a metal component may be such that the amount of the metal component is about 0.01 to about 10 times the stoichiometric amount, and preferably about 0.1 to about 5 times the stoichiometric amount.

More specifically, when a fluorine-containing sulfonyl halide of general formula (1) is used as a starting material, and an alkali metal halide is used as a metal halide $M^1X$, the alkali metal halide may be used in an amount of about 0.1 to about 10 moles, and preferably about 1 to about 5 moles, per mole of the fluorine-containing sulfonyl halide. When an alkaline earth metal halide is used as a metal halide $M^1X$, the alkali metal halide may be used in an amount of about 0.05 to about 5 moles, and preferably about 0.5 to about 2.5 moles, per mole of the fluorine-containing sulfonyl halide.

When a starting fluorine-containing sulfonyl chloride of general formula (1') is reacted with a metal component, the metal component may be used in an amount of about 0.01 to about 10 moles, and preferably about 0.1 to about 5 moles, per mole of the fluorine-containing sulfonyl chloride.

When a fluorine-containing disulfonyl chloride of general formula (2) is used as a starting material, and an alkali metal halide is used as a metal halide $M^1X$, the alkali metal halide may be used in an amount of about 0.2 to about 20 moles, and preferably about 2 to about 10 moles, per mole of the fluorine-containing disulfonyl chloride. When an alkaline earth metal halide is used as a metal halide $M^1X$, the alkaline earth metal halide may be used in an amount of about 0.1 to about 10 moles, and preferably about 1 to about 5 moles, per mole of the fluorine-containing disulfonyl chloride.

When a fluorine-containing disulfonyl chloride of general formula (2) as a starting material is reacted with a metal component, the metal component may be used in an amount of about 0.02 to about 20 moles, and preferably about 0.2 to about 10 moles, per mole of the fluorine-containing disulfonyl chloride.

These reactions may be carried out in the presence or absence of a solvent. The reactions are preferably carried out in a solvent in order to remove the heat of reaction, and increase the reaction rate. Examples of usable solvents include polar solvents, such as water, dimethyl sulfoxide (DMSO), N,N-dimethylformamide (DMF), sulfolane, $CH_3CN$, $CHCl_3$ and the like; nonpolar solvents, such as $CH_2Cl_2$, $C_6F_{14}$ and the like; etc. Polar solvents are preferably used.

The amount of solvent used is preferably about 0.01 to about 100 times by volume that of the starting fluorine-containing sulfonyl halide or fluorine-containing disulfonyl chloride, and more preferably about 0.1 to about 10 times that by volume.

The reaction temperature may be within a broad range, i.e, from about −20 to about 200° C., and preferably from about 10 to about 70° C.

The reactions may be carried out under reduced pressure, under atmospheric pressure or under applied pressure, and preferably under atmospheric pressure.

The reaction time is typically from about 0.01 to about 48 hours, and preferably about 0.5 to about 24 hours.

Target fluorine-containing halides can be obtained in the manner as described above.

The fluorine-containing halides obtained are as follows.

When a fluorine-containing sulfonyl halide represented by general formula (1) is used as a starting material and reacted with a metal halide, a fluorine-containing bromide or fluorine-containing iodide is obtained represented by general formula shown below:

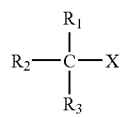

wherein $R_1$, $R_2$, $R_3$ and X are the same as above.

When a fluorine-containing sulfonyl chloride represented by general formula (1') is used as a starting material and reacted with a metal component, a fluorine-containing chloride is obtained represented by general formula shown below:

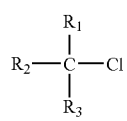

wherein $R_1$, $R_2$ and $R_3$ are the same as above.

When a fluorine-containing disulfonyl chloride represented by general formula (2) is used as a starting material and reacted with a metal halide, a fluorine-containing bromide or fluorine-containing iodide is obtained represented by general formula shown below:

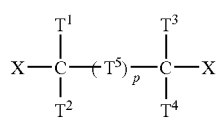

wherein $T^1$, $T^2$, $T^3$, $T^4$, $T^5$, X and p are the same as above; and when such a fluorine-containing disulfonyl chloride is reacted with a metal component, a fluorine-containing chloride is obtained represented by general formula shown below:

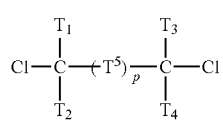

wherein $T^1$, $T^2$, $T^3$, $T^4$, $T^5$ and p are the same as above.

Crude compounds obtained in the method of the present invention are in the form of homogeneous or separated solutions. The target fluorine-containing halides can be obtained by purifying these crude compounds by conventional processes, such as separation, filtration, distillation, column chromatography and the like.

Fluorine-containing chloride, fluorine-containing bromide and fluorine-containing iodide thus produced are useful as the intermediates for, e.g., chemicals, pharmaceuticals, agrochemicals, resins and the like.

Effects of the Invention

According to the method of the present invention, the target fluorine-containing chlorides, fluorine-containing bromides and fluorine-containing iodides can be prepared in good yields at low cost, using industrially advantageous processes without requiring complicated operations.

BEST MODE FOR CARRYING OUT THE INVENTION

The present invention is now described in further details through the following Examples.

Example 1

In a 100 ml three-neck flask equipped with a Dimroth condenser and a dropping funnel were placed 30 g of DMSO and 30.4 g (202.4 mmol) of NaI. Through the dropping funnel was added dropwise 20.0 g (67.5 mmol) of $CF_2$=$CFOCF_2CF_2SO_2Cl$, with stirring at room temperature (23.0° C.). During the dropwise addition, the solution was heated by self-heating to a maximum of 85° C., and changed its color from colorless to reddish brown.

After the completion of dropwise addition, the solution was further reacted with stirring for 1.5 hours. After the completion of reaction, the solution was separated into two phases by addition of water and $CCl_4$, and the organic $CCl_4$ phase was analyzed by gas chromatography and $^{19}F$-NMR. As a result, the formation of the target compound $CF_2$=$CFOCF_2CF_2I$ was confirmed.

The $CF_2$=$CFOCF_2CF_2SO_2Cl$ conversion ratio was 100.0%; $CF_2$=$CFOCF_2CF_2I$ selectivity was 99% or more; and $CF_2$=$CFOCF_2CF_2I$ yield was 99.9% or more.

Example 2

In a 100-ml three neck flask equipped with a Dimroth condenser and a dropping funnel were placed 30 g of DMSO and 20.3 g (197.3 mmol) of NaBr. Through the dropping funnel was added dropwise 20.0 g (65.9 mmol) of $CF_2$=$CFOCF_2CF_2SO_2Cl$ with 97.8 mass % purity, with stirring at room temperature (21.0° C.). During the dropwise addition, the solution was heated by self-heating to a maximum of 52° C., and changed its color from colorless to yellow.

After the completion of dropwise addition, the solution was further reacted with stirring for 1.5 hours. After the completion of reaction, the solution was separated into two phases by addition of water, and the organic phase was analyzed by gas chromatography and $^{19}F$-NMR. As a result, the formation of the target compound $CF_2$=$CFOCF_2CF_2Br$ was confirmed.

The $CF_2$=$CFOCF_2CF_2SO_2Cl$ conversion ratio was 88.2%; $CF_2$=$CFOCF_2CF_2Br$ selectivity was 99% or more; and $CF_2$=$CFOCF_2CF_2Br$ yield was 68.6%.

Example 3

In a 100 ml three neck flask equipped with a Dimroth condenser were placed 30 g of DMF and 20.9 g (204.9 mmol) of NaBr. Then, 10.0 g (17.8 mmol) of solid $ClO_2S(CF_2CF_2)_2SO_2Cl$ with 71.0 mass % purity was added in portions to the solution, with stirring at room temperature (21.0° C.).

Although the addition was not exothermic, after the completion of addition, the solution was heated by self-heating to a maximum of 50° C., and changed its color from colorless to yellow.

After the completion of addition, the solution was further reacted with stirring for 1.5 hours. After the completion of reaction, the solution was separated into two phases by addition of water, and the organic phase was analyzed by gas chromatography and $^{19}F$-NMR. As a result, the formation of the target material $Br(CF_2CF_2)_2Br$ was confirmed.

The $ClO_2S(CF_2CF_2)_2SO_2Cl$ conversion ratio was 100%; $Br(CF_2CF_2)_2Br$ selectivity was 99% or more; and $Br(CF_2CF_2)_2Br$ yield was 78.1%.

Example 4

In a 10 ml glass sample bottle were placed 0.1 g (1.01 mmol) of CuCl, 1.09 g of DMF, and 0.19 g (1.02 mmol) of hexafluorobenzene (internal standard). To the mixture was added at room temperature 0.24 g (0.79 mmol) of $CF_2$=$CFOCF_2CF_2SO_2Cl$ with 97.8 mass % purity. After the completion of addition, the solution was reacted with stirring for 2 hours at room temperature. After the completion of reaction, the solution was separated into two phases by addition of water, and the organic phase was analyzed by gas chromatography and $^{19}F$-NMR. As a result, the formation of the target compound $CF_2$=$CFOCF_2CF_2Cl$ was confirmed.

The $CF_2$=$CFOCF_2CF_2SO_2Cl$ conversion ratio was 100.0%; $CF_2$=$CFOCF_2CF_2Cl$ selectivity was 99% or more; and $CF_2$=$CFOCF_2CF_2Cl$ yield was 51.9%.

Example 5

In a 100 ml flask were placed 30 g of DMSO and 16.1 g (107.1 mmol) of NaI. Then, 10.0 g (35.7 mmol) of $CF_2$=$CFOCF_2CF_2SO_2F$ was added dropwise to the solution with stirring at room temperature. After the completion of dropwise addition, the solution was reacted for 2 hours with heating to 75 to 110° C. After the completion of reaction, the solution was quenched in water and separated, and then the bottom layer was collected.

An analysis using GC/MS and $^{19}F$-NMR confirmed the formation of $CF_2$=$CFOCF_2CF_2I$. The $CF_2$=$CFOCF_2CF_2SO_2F$ conversion ratio was 100%, and $CF_2$=$CFOCF_2CF_2I$ yield was 60.0%.

The invention claimed is:

1. A method for producing a fluorine-containing halide, comprising reacting a fluorine-containing sulfonyl halide with a metal halide in the presence or absence of a solvent, the fluorine-containing sulfonyl halide being represented by general formula (1):

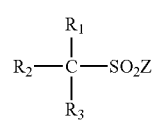

(1)

wherein $R^1$, $R^2$ and $R^3$ are the same or different, each representing a halogen atom, a hydrogen atom or a monovalent hydrocarbon group which may contain one or more atoms of one or more kinds selected from fluorine, oxygen, nitrogen and sulfur atoms; at least one of $R^1$, $R^2$ and $R^3$ is a halogen atom; Z is Cl or F; provided that when none of $R^1$, $R^2$ and $R^3$ is a fluorine atom, at least one of $R^1$, $R^2$ and $R^3$ is a monovalent fluorine-containing hydrocarbon group, and when Z is F, $R_1$ and $R_3$ are both fluorine atoms and $R_2$ is a $CF_2$=$CFOCF_2$— group;

the metal halide being represented by general formula $M^1X$, wherein $M^1$ is Ma or $(Mb)_{1/2}$, Ma being an alkali metal, Mb being an alkaline earth metal, and X being Br or I;

the fluorine-containing halide being represented by the general formula shown below:

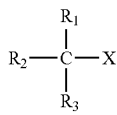

wherein $R_1$, $R_2$, $R_3$ and X are the same as above.

2. The method for producing a fluorine-containing halide according to claim 1, wherein the fluorine-containing sulfonyl halide represented by general formula (1) is a compound represented by general formula (1a):

$$R^4CF_2SO_2Cl \quad (1a)$$

wherein $R^4$ is a halogen atom, a hydrogen atom or a monovalent hydrocarbon group which may contain one or more atoms of one or more kinds selected from fluorine, oxygen, nitrogen and sulfur atoms.

3. The method for producing a fluorine-containing halide according to claim 1, wherein the fluorine-containing sulfonyl halide represented by general formula (1) is a compound represented by general formula $Y(CF_2)_n$—$SO_2Cl$ wherein Y is a halogen atom, —$SO_2F$ or —$CCl_3$, and n is an integer from 1 to 9; a compound represented by general formula $CF_2$=$CF(CF_2)_e(OCF_2CF(CF_3))_gO(CF_2)_h$—$SO_2Cl$ wherein e is an integer from 0 to 2, g is an integer from 0 to 3, and h is an integer from 1 to 6; or a compound represented by general formula $CF_2$=$CFOCF_2CF_2SO_2F$.

4. The method according to claim 1, wherein the metal halide represented by chemical formula $M^1X$ is an alkali metal bromide or alkali metal iodide.

5. The method according to claim 1, wherein the reaction is carried out in a polar solvent.

6. A method for producing a fluorine-containing chloride, comprising reacting a fluorine-containing sulfonyl chloride in the presence or absence of a solvent with at least one member selected from the group consisting of metals belonging to periods 4 to 7 of groups 3 to 16 in the periodic table and compounds containing any of such metals, the fluorine-containing sulfonyl chloride being represented by general formula (1'):

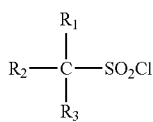

wherein $R^1$, $R^2$ and $R^3$ are the same or different, each representing a halogen atom, a hydrogen atom or a monovalent hydrocarbon group which may contain one or more atoms of one or more kinds selected from fluorine, oxygen, nitrogen and sulfur atoms; and at least one of $R^1$, $R^2$ and $R^3$ is a halogen atom; provided that when none of $R^1$, $R^2$ and $R^3$ is a fluorine atom, at least one of $R^1$, $R^2$ and $R^3$ is a monovalent fluorine-containing hydrocarbon group;

the fluorine-containing chloride being represented by the general formula shown below:

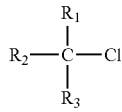

wherein $R^1$, $R^2$ and $R^3$ are the same as above.

7. The method for producing a fluorine-containing chloride according to claim 6, wherein the fluorine-containing sulfonyl chloride represented by general formula (1') is a compound represented by general formula (1a):

$$R^4CF_2SO_2Cl \quad (1a)$$

wherein $R^4$ is a halogen atom, a hydrogen atom or a monovalent hydrocarbon group which may contain one or more atoms of one or more kinds selected from fluorine, oxygen, nitrogen and sulfur atoms.

8. The method for producing a fluorine-containing chloride according to claim 6, wherein the fluorine-containing sulfonyl chloride represented by general formula (1') is a compound represented by general formula $Y(CF_2)_n$—$SO_2Cl$ wherein Y is a halogen atom, —$SO_2F$ or —$CCl_3$, and n is an integer from 1 to 9; or a compound represented by general formula $CF_2$=$CF(CF_2)_e(OCF_2CF(CF_3))_gO(CF_2)_h$—$SO_2Cl$ wherein e is an integer from 0 to 2, g is an integer from 0 to 3, and h is an integer from 1 to 6.

9. The method according to claim 6, wherein the metals belonging to periods 4 to 7 of groups 3 to 16 in the periodic table are Cu, Pt, Pd, Ni, Zn and Fe, and the compounds containing any of metals belonging to periods 4 to 7 of groups 3 to 16 in the periodic table are compounds containing Cu, Fe, Ni, Co, Pd, Ti or Pb as a metal component.

10. The method according to claim 6, wherein the reaction is carried out in a polar solvent.

11. A method for producing a fluorine-containing halide, comprising reacting a fluorine-containing disulfonyl chloride with a metal halide in the presence or absence of a solvent, the fluorine-containing disulfonyl chloride being represented by general formula (2):

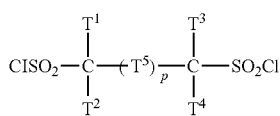

wherein $T^1$, $T^2$, $T^3$ and $T^4$ are the same or different, each representing a halogen atom, a hydrogen atom or a monovalent hydrocarbon group which may contain one or more atoms of one or more kinds selected from fluorine, oxygen, nitrogen and sulfur atoms; at least one of $T^1$, $T^2$, $T^3$ and $T^4$ is a halogen atom; $T^5$ is a bivalent hydrocarbon group which may contain one or more atoms of one or more kinds selected from fluorine, oxygen, nitrogen and sulfur atoms; and p is 0 or 1; provided that at least one of $T^1$ and $T^2$ is a monovalent fluorine-containing hydrocarbon group when neither $T^1$ nor $T^2$ is a fluorine atom, and at least one of $T^3$ and $T^4$ is a monovalent fluorine-containing hydrocarbon group when neither $T^3$ nor $T^4$ is a fluorine atom;

the metal halide being represented by general formula $M^1X$, wherein $M^1$ is Ma or $(Mb)_{1/2}$, Ma being an alkali metal, Mb being an alkaline earth metal, and X being Br or I;

the fluorine-containing halide being represented by general formula shown below:

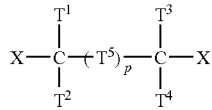

wherein $T^1$, $T^2$, $T^3$, $T^4$, $T^5$, X and p are the same as above.

12. The method for producing a fluorine-containing halide according to claim 11, wherein the fluorine-containing disulfonyl chloride represented by general formula (2) is a compound represented by general formula (2a):

$$ClSO_2\text{—}F_2C\text{-}(T^5)_p\text{-}CF_2\text{—}SO_2Cl \qquad (2a)$$

wherein $T^5$ is a bivalent hydrocarbon group which may contain one or more atoms of one or more kinds selected from fluorine, oxygen, nitrogen and sulfur atoms; and p is 0 or 1.

13. The method for producing a fluorine-containing halide according to claim 11, wherein the fluorine-containing disulfonyl chloride represented by general formula (2) is a compound represented by general formula $ClSO_2(CF_2)_pSO_2Cl$, wherein p is an integer from 2 to 9.

14. The method according to claim 11, wherein the metal halide represented by chemical formula $M^1X$ is an alkali metal bromide or alkali metal iodide.

15. The method according to claim 11, wherein the reaction is carried out in a polar solvent.

16. A method for producing a fluorine-containing chloride, comprising reacting a fluorine-containing disulfonyl V chloride in the presence or absence of a solvent with at least one member selected from the group consisting of metals belonging to periods 4 to 7 of groups 3 to 16 in the periodic table and compounds containing any of such metals, the fluorine-containing disulfonyl chloride being represented by general formula (2):

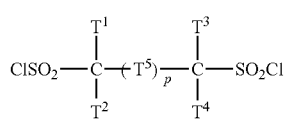

wherein $T^1$, $T^2$, $T^3$ and $T^4$ are the same or different, each representing a halogen atom, a hydrogen atom or a monovalent hydrocarbon group which may contain one or more atoms of one or more kinds selected from fluorine, oxygen, nitrogen and sulfur atoms; at least one of $T^1$, $T^2$, $T^3$ and $T^4$ is a halogen atom; $T^5$ is a bivalent hydrocarbon group which may contain one or more atoms of one or more kinds selected from fluorine, oxygen, nitrogen and sulfur atoms; and p is 0 or 1; provided that at least one of $T^1$ and $T^2$ is a monovalent fluorine-containing hydrocarbon group when neither $T^1$ nor $T^2$ is a fluorine atom, and at least one of $T^3$ and $T^4$ is a monovalent fluorine-containing hydrocarbon group when neither $T^3$ nor $T^4$ is a fluorine atom;

the fluorine-containing chloride being represented by general formula shown below:

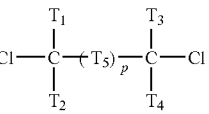

wherein $T^1$, $T^2$, $T^3$, $T^4$, $T^5$ and p are the same as above.

17. The method for producing a fluorine-containing chloride according to claim 16, wherein the fluorine-containing disulfonyl chloride represented by general formula (2) is a compound represented by general formula (2a):

$$ClSO_2\text{—}F_2C\text{-}(T^5)_p\text{-}CF_2\text{—}SO_2Cl \qquad (2a)$$

wherein $T^5$ is a bivalent hydrocarbon group which may contain one or more atoms of one or more kinds selected from fluorine, oxygen, nitrogen and sulfur atoms; and p is 0 or 1.

18. The method for producing a fluorine-containing chloride according to claim 16, wherein the fluorine-containing disulfonyl chloride represented by general formula (2) is a compound represented by general formula $ClSO_2(CF_2)_p SO_2Cl$, wherein p is an integer from 2 to 9.

19. The method according to claim 16, wherein the metals belonging to periods 4 to 7 of groups 3 to 16 in the periodic table are Cu, Pt, Pd, Ni, Zn and Fe, and the compounds containing any of metals belonging to periods 4 to 7 of groups 3 to 16 in the periodic table are compounds containing Cu, Fe, Ni, Co, Pd, Ti or Pb as a metal component.

20. The method according to claim 16, wherein the reaction is carried out in a polar solvent.

\* \* \* \* \*